United States Patent
Ogihara et al.

(10) Patent No.: US 7,922,683 B2
(45) Date of Patent: Apr. 12, 2011

(54) EXTRACORPOREAL CIRCULATOR

(75) Inventors: Mitsuaki Ogihara, Shizuoka (JP);
Hidetaka Nakayama, Shizuoka (JP);
Kazuhiko Takeuchi, Shizuoka (JP);
Yuki Ishikura, Shiga (JP); Akiyasu Ito,
Kanagawa (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 822 days.

(21) Appl. No.: 11/632,828

(22) PCT Filed: Jul. 21, 2005

(86) PCT No.: PCT/JP2005/013405
§ 371 (c)(1),
(2), (4) Date: Sep. 19, 2007

(87) PCT Pub. No.: WO2006/009214
PCT Pub. Date: Jan. 26, 2006

(65) Prior Publication Data
US 2008/0221498 A1 Sep. 11, 2008

(30) Foreign Application Priority Data
Jul. 22, 2004 (JP) .................. 2004-214968

(51) Int. Cl.
*A61M 37/00* (2006.01)
(52) U.S. Cl. ............ 604/6.15; 604/4.01; 604/6.09; 604/6.1; 604/6.11
(58) Field of Classification Search ............ 604/4.01, 604/5.01, 5.04, 6.09, 6.11, 507, 508, 8, 9
See application file for complete search history.

(56) References Cited

U.S. PATENT DOCUMENTS

| 4,397,747 | A | 8/1983 | Ikeda |
| 5,851,202 | A | 12/1998 | Carlsson |
| 6,302,860 | B1 * | 10/2001 | Gremel et al. ........... 604/6.09 |
| 2004/0197223 | A1 * | 10/2004 | Olsen et al. ............. 422/45 |
| 2007/0110612 | A1 | 5/2007 | Ito |

FOREIGN PATENT DOCUMENTS

| JP | 57-022763 | 2/1982 |
| JP | 64-8562 A | 1/1989 |
| JP | 1-148265 A | 6/1989 |
| JP | 2-131771 A | 5/1990 |
| JP | 8-510812 A | 11/1996 |
| JP | 10-505518 A | 6/1998 |
| JP | 2593761 Y2 | 4/1999 |
| WO | 02/064191 A1 | 8/2002 |

OTHER PUBLICATIONS

International Search Report dated Oct. 25, 2005.
Translation of the International Preliminary Report on Patentability.

* cited by examiner

*Primary Examiner* — Leslie R Deak
(74) *Attorney, Agent, or Firm* — Buchanan Ingersoll & Rooney PC (57) ABSTRACT

An extracorporeal circulator comprising a line for extracting blood from a patient, a pump for supplying blood, an artificial lung section performing gas exchange on blood, a line for supplying blood passed through the artificial lung section to the patient, a unit for removing bubbles mixed into the blood, a controller for controlling the flow rate of blood being supplied such that bubbles are not fed to the patient, and a line for detouring blood delivered from the blood pump to return it to the blood pump.

6 Claims, 8 Drawing Sheets

EXTRACORPOREAL CIRCULATOR

TECHNICAL FIELD

The present invention relates to an extracorporeal circulator comprising a blood pump for transferring blood to circulate it extracorporeally, a bubble removing unit for removing bubbles in the extracorporeally circulating blood, and means for controlling the operation of the blood pump.

BACKGROUND ART

For example, during cardiac surgeries, artificial-lung extracorporeal circulation is generally performed in which patient's blood is drawn from the vein (the vena cava) of the patient by a blood pump, and the gas is exchanged by an artificial lung, and then the blood is returned to the artery of the patient.

A circuit for such extracorporeal circulation (an extracorporeal circulation circuit) is equipped with a bubble removing unit for removing (separating) bubbles flowing in the drawn blood. Known bubble removing units include a unit including a housing (container body) and a filter disposed in the housing and partitioning the housing into a blood inflow space (upper space) into which blood flows and a blood outflow space (lower space) from which blood flows out, which applies centrifugal force to the blood to collect bubbles into the center of the housing (blood inflow space) and collects the bubbles to the upper space of the housing by buoyancy, and then removes the bubbles with deaeration means (for example, refer to JP-B-64-8562).

However, with the bubble removing unit, when excessive bubbles (gas) accumulate in the blood inflow space (bubble reservoir), the bubbles sometimes pass through the filter, posing the possibility that the bubbles are not sufficiently (completely) removed, so that they may flow out of the bubble removing unit together with the filtered blood.

DISCLOSURE OF THE INVENTION

It is an object of the invention to provide an extracorporeal circulator in which bubbles mixed into the blood can be reliably prevented from being fed to the patient with reduced priming volume.

An extracorporeal circulator according to the invention is characterized by comprising: an venous line for drawing blood from a patient; a blood pump for feeding the blood; an artificial lung that performs gas exchange of the blood; an arterial line for feeding the blood that has passed through the artificial lung to the patient; a bubble removing unit that removes the bubbles mixed in the blood; blood-feed control means for controlling the amount of blood being fed so as not to feed the bubbles to the patient; and a bypass line for bypassing the blood discharged from the blood pump and returning the blood to the blood pump.

This arrangement can reliably prevent bubbles mixed in the blood from being fed to the patient while reducing the priming volume.

In the extracorporeal circulator according to the invention, preferably, the bubble removing unit comprises: a circulation-flow forming chamber including an inner space having a substantially circular cross section; an inlet disposed substantially tangential to the inner periphery of the circulation-flow forming chamber, for introducing the blood into the circulation-flow forming chamber so that the blood forms a circulation flow in the circulation-flow forming chamber; an outlet disposed at the lower part of the circulation-flow forming chamber; and a bubble reservoir disposed on the circulation-flow forming chamber, for temporarily storing the bubbles rising from the circulation-flow forming chamber.

This arrangement allows effective use of the bubble separation effect of the centrifugal force and the buoyancy of the circulation flow, providing high bubble removing capability.

In the extracorporeal circulator according to the invention, preferably, the bubble reservoir further comprises: a vacuum chamber disposed on the bubble reservoir and connected to deaerator means to be maintained at a negative pressure; a first filter disposed to partition the bubble reservoir and the vacuum chamber from each other and allowing the passage of gas and rejects the passage of blood; and a second filter disposed between the vacuum chamber and the deaerator means and allowing the passage of gas and rejects the passage of liquid.

This arrangement can reliably prevent the liquid that has passed through the first filter (for example, condensation of water vapor) from flowing to the outside with the second filter.

In the extracorporeal circulator according to the invention, preferably, the bubble removing unit is disposed between the first filter and the second filter and includes a liquid reservoir capable of storing liquid flowing out of the vacuum chamber.

This arrangement ensures collection of the liquid in the liquid reservoir, thus reliably preventing the liquid from flowing to the outside.

In the extracorporeal circulator according to the invention, preferably, the bubble removing unit includes bubble detection means for detecting the bubbles; and the blood-feed control means controls the operation of the blood pump according to the detection result of the bubble detection means.

This arrangement reliably prevents bubbles from excessively accumulating in the extracorporeal circulator to allow smooth and appropriate extracorporeal circulation, and reliably prevents the bubbles mixed in the extracorporeal circuit from being fed to the patient while reducing the priming volume.

In the extracorporeal circulator according to the invention, preferably, the bubble detection means includes at least one sensor for detecting the fluid level of the blood in the bubble reservoir or information thereon.

This arrangement reliably prevents bubbles from excessively accumulating in the bubble reservoir to allow smooth and appropriate extracorporeal circulation, and reliably prevents the bubbles mixed in the extracorporeal circuit from being fed to the patient while decreasing the priming volume.

In the extracorporeal circulator according to the invention, preferably, the sensor includes a first sensor for detecting a first fluid level of the blood and a second sensor for detecting a second fluid level lower than the first fluid level.

This arrangement reliably prevents bubbles from excessively accumulating in the bubble reservoir to allow smooth and appropriate extracorporeal circulation, and reliably prevents the bubbles mixed in the extracorporeal circuit from being fed to the patient while decreasing the priming volume.

In the extracorporeal circulator according to the invention, preferably, the blood-feed control means controls the operation of the blood pump according to the information obtained from the first sensor and the second sensor.

This arrangement reliably prevents bubbles from excessively accumulating in the bubble reservoir to allow smooth and appropriate extracorporeal circulation, and reliably prevents the bubbles mixed in the extracorporeal circuit from being fed to the patient while decreasing the priming volume.

In the extracorporeal circulator according to the invention, preferably, when the first sensor detects that the fluid level of the blood has reached the first fluid level, the blood-feed control means controls the operation of the blood pump so as to decrease the rate of blood feed.

This arrangement more reliably prevents bubbles from excessively accumulating in the bubble reservoir to allow smooth and appropriate extracorporeal circulation.

In the extracorporeal circulator according to the invention, preferably, when the first sensor detects that the fluid level of the blood has reached the first fluid level from a position between the first fluid level and the second fluid level, the blood-teed control means controls the blood pump to maintain the operating state at that time.

This arrangement more reliably prevents bubbles from excessively accumulating in the bubble reservoir to allow smooth and appropriate extracorporeal circulation In the extracorporeal circulator according to the invention, preferably, when the second sensor detects that the fluid level of the blood has reached the second fluid level, the blood-feed control means controls the blood to recirculate between the blood pump and the bypass line.

This arrangement reliably prevents the bubbles in the bubble removing unit from being fed to the patient and decreases the damage to the blood in the blood pump even when the blood pump continuously operates.

In the extracorporeal circulator according to the invention, preferably, when the first sensor detects that the fluid level of the blood in the bubble reservoir has reached the first fluid level during blood recirculation, the blood-feed control means stops the blood recirculation and controls the blood so as to pass through the venous line, the blood pump, the artificial lung, the arterial line, and the bubble removing unit.

This arrangement allows repeated gas exchange for the heart of a patient.

In the extracorporeal circulator according to the invention, preferably, when the second sensor detects that the fluid level of the blood has reached the second fluid level, the blood-feed control means controls the blood pump to stop the operation.

This arrangement more reliably prevents bubbles from excessively accumulating in the bubble reservoir.

In the extracorporeal circulator according to the invention, preferably, the first sensor and/or the second sensor includes a transmitter for transmitting ultrasonic waves and a receiver for receiving the transmitted ultrasonic waves, and can detect the fluid level of the blood in the bubble reservoir using the difference between the transmittance of ultrasonic waves passing through blood and the transmittance of the ultrasonic waves passing through gas.

This arrangement ensures detection of the fluid level of the blood.

In the extracorporeal circulator according to the invention, preferably, the bottom of the bubble reservoir has a slope out of the horizontal, and the first sensor and the second sensor are disposed along the inclination of the slope of the bubble reservoir.

This arrangement ensures detection of changes in fluid level as the blood flows along the slope.

In the extracorporeal circulator according to the invention, preferably, the first sensor is disposed in the vicinity of the upper part of the slope of the bubble reservoir.

This arrangement further ensures detection of changes in fluid level as the blood flows along the slope.

In the extracorporeal circulator according to the invention, preferably, the first sensor and the second sensor are vertically separate from each other by 3 to 30 mm.

When the clearance is less than the lower limit, the first sensor and the second sensor are too close to each other. Accordingly, after the first sensor senses the first fluid level, the second sensor senses the second fluid level soon to control the operation of the blood pump. This sometimes extremely reduces the operability of the extracorporeal circulator. On the other hand, when the clearance exceeds the upper limit, the second sensor may be located lower than the bubble reservoir depending on other conditions (for example, when the bubble reservoir is small). This sometimes makes it impossible for the second sensor to detect the second fluid level in the bubble reservoir.

In the extracorporeal circulator according to the invention, preferably, the bubble removing unit has a truncated conical portion at the upper part of the circulation-flow forming chamber, the inside diameter of the truncated conical portion decreasing gradually upward.

This arrangement ensures that the blood mixed in the bubble removing unit forms a circulation flow.

In the extracorporeal circulator according to the invention, preferably, the bubble removing unit further comprises: a first communicating section for communicating the vicinity of the top of the circulation-flow forming chamber with the bubble reservoir to allow the bubbles rising from the circulation-flow forming chamber to pass through; and a second communicating section for communicating the vicinity of the peripheral wall of the circulation-flow forming chamber with the bubble reservoir, wherein the bubbles rising from the circulation-flow forming chamber flow into the bubble reservoir through the first communicating section and the blood in the bubble reservoir is returned to the circulation-flow forming chamber through the second communicating section.

This arrangement allows the bubbles in the circulation-flow forming chamber to be introduced into the bubble reservoir smoothly and quickly.

In the extracorporeal circulator according to the invention, preferably, the blood pump is a centrifugal pump, in which the rate of blood feed is increased or decreased by increasing or decreasing the rotation speed of the centrifugal pump.

This arrangement facilitates controlling the rate of blood feed.

In the extracorporeal circulator according to the invention, preferably, the rotation speed is controlled so as to increase or decrease continuously or stepwise.

When the rotation speed is controlled so as to decrease continuously, the rotation speed of the pump can be decreased quickly in a state in which the amount of inflow bubbles significantly exceeds the bubble removing capacity. Thus, the extracorporeal circulation can be maintained without the need for stopping the blood pump. In contrast, when the rotation speed is controlled so as to decrease stepwise, the time to recover the fluid level (from falling to rising) is given in a state in which the amount of inflow bubbles a little exceeds the bubble removing capacity. This eliminates the need for excessively decreasing the rotation speed of the blood pump.

In the extracorporeal circulator according to the invention, preferably, the bubble removing unit is disposed upstream from the blood pump.

This arrangement can prevent the bubbles mixed in the blood from being broken into small pieces by the blood pump, allowing separation and removal of the bubbles from the blood more reliably.

In the extracorporeal circulator according to the invention, preferably, the artificial lung is disposed between the outlet through which the blood in the blood pump is discharged and an inlet into which the blood in the bypass line flows.

This arrangement ensures gas exchange for the blood recirculating between the blood pump and the bypass line.

BEST MODE FOR CARRYING OUT THE INVENTION

An extracorporeal circulator according to the invention will be described in detail below on the basis of preferred embodiments shown in the accompanying drawings.

First Embodiment

Figure 1:
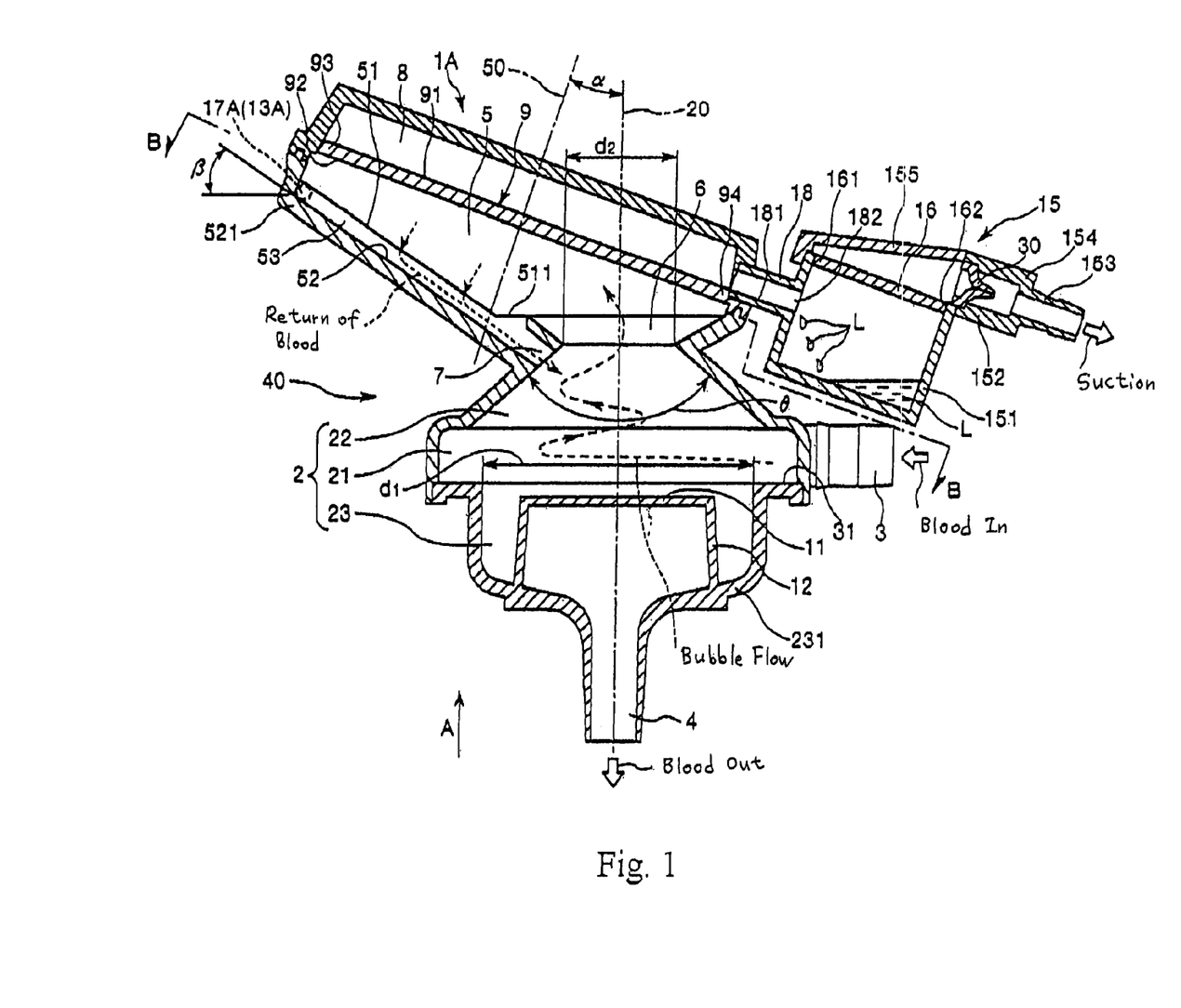
FIG. 1 is a cross-sectional side view of a bubble removing unit of an extracorporeal circulator (a first embodiment) of the invention.
Figure 2:
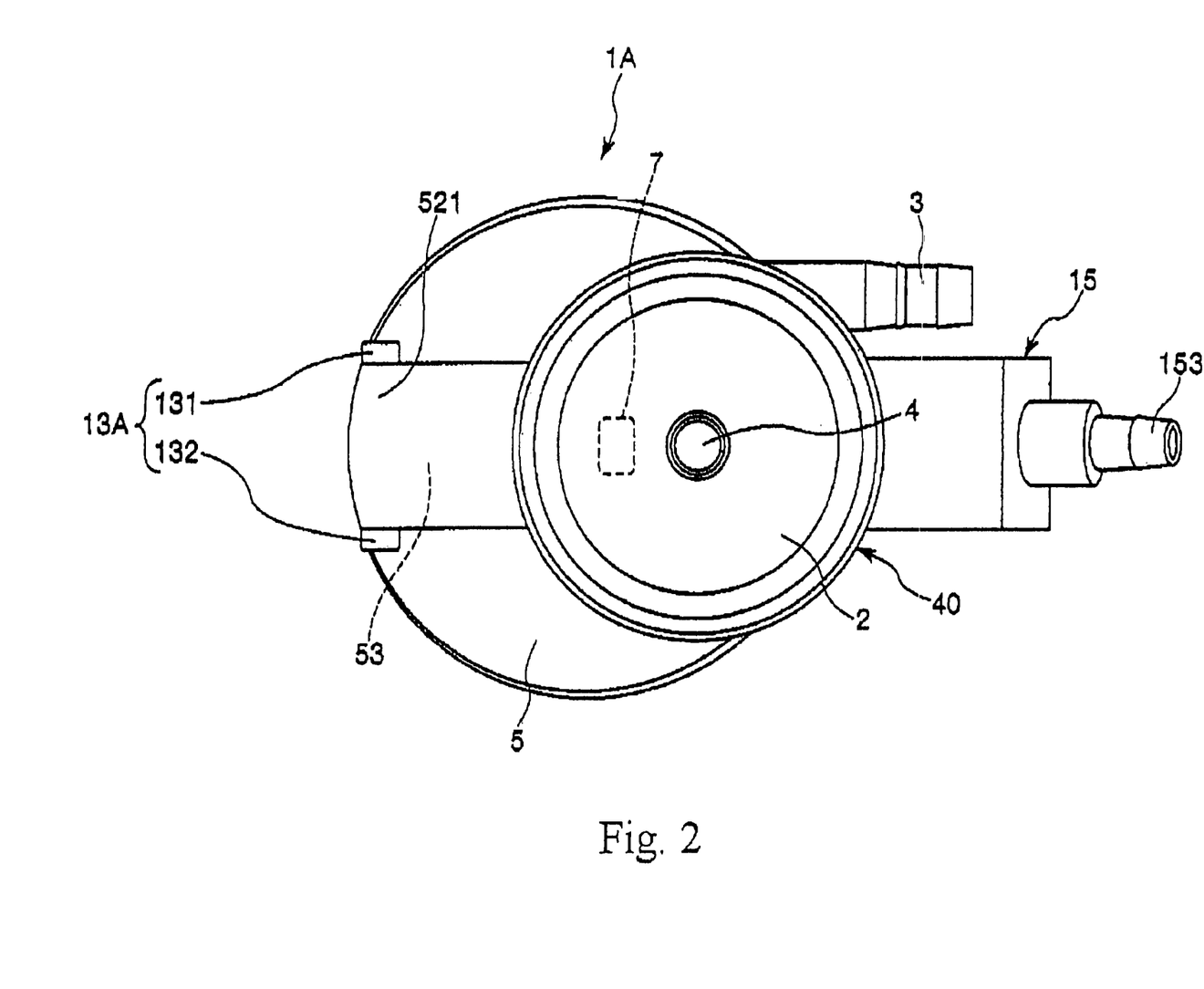
FIG. 2 is an arrow diagram (bottom view) of the unit taken on arrow A of FIG. 1
Figure 3:
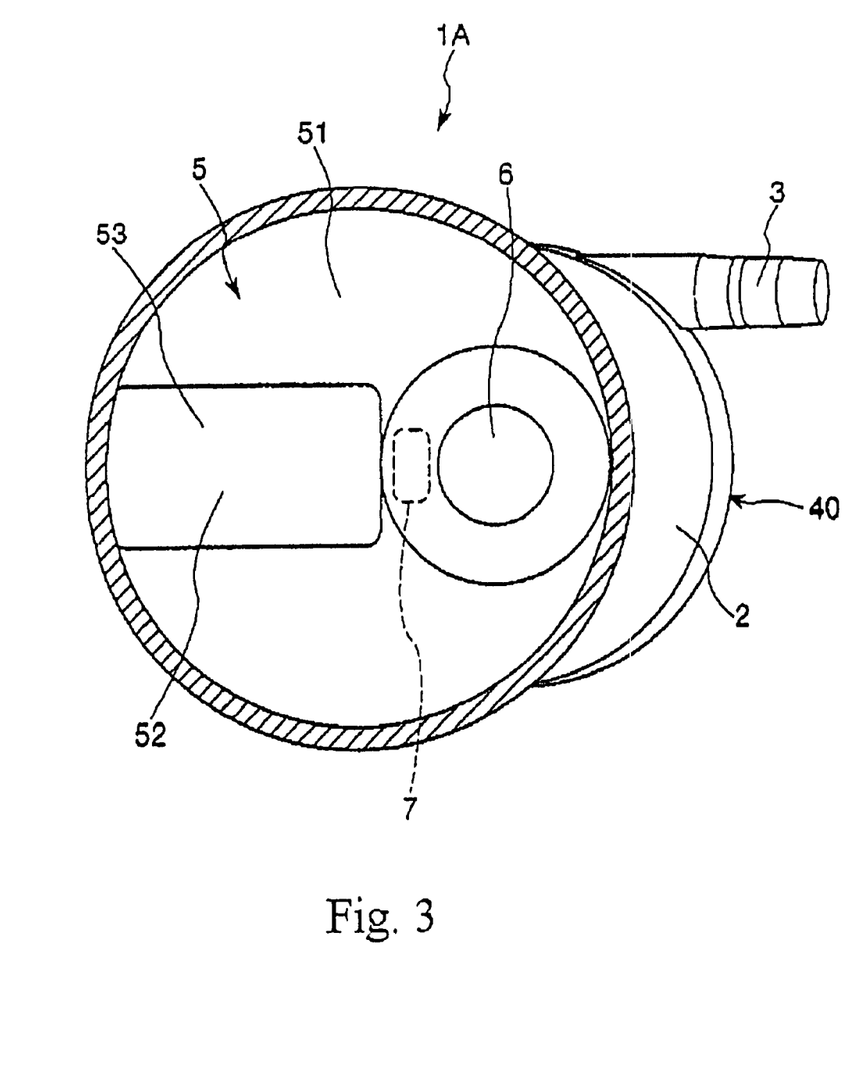
FIG. 3 is a sectional view of the unit taken along line B-B of FIG. 1.
Figure 4:
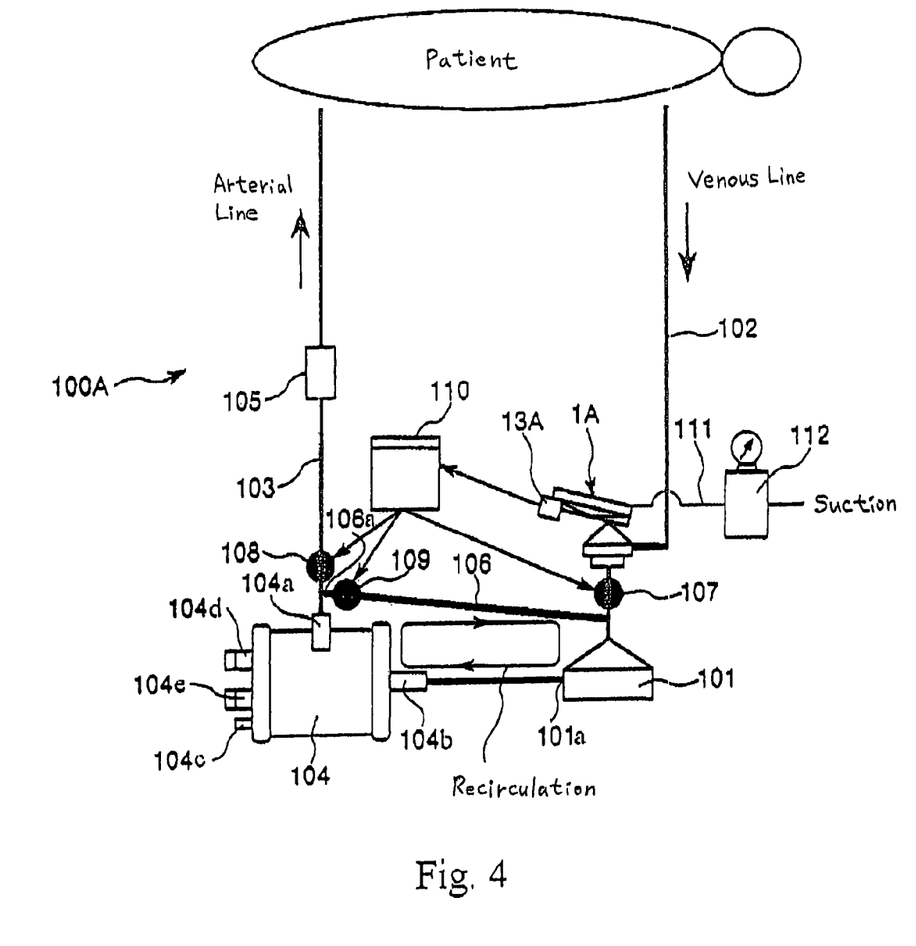
FIG. 4 is a schematic diagram of the extracorporeal circulator of the first embodiment of the invention.

FIG. 1 is a cross-sectional side view of a bubble removing unit of an extracorporeal circulator (a first embodiment) of the invention; FIG. 2 is an arrow diagram (bottom view) of the unit taken on arrow A of FIG. 1; FIG. 3 is a sectional view of the unit taken along line B-B of FIG. 1; and FIG. 4 is a schematic diagram of the extracorporeal circulator of the first embodiment of the invention. The upper part in FIG. 1 is referred to as "the upper part" or "above", and the lower part is referred to as "the lower part" or "below" for the convenience of description.

A bubble removing unit 1A of an extracorporeal circulator 100A will first be described.

The bubble removing unit 1A in the drawings is for removing the bubbles (gas) in the blood circulating extracorporeally. The bubble removing unit 1A can be used in both an extracorporeal circulation in which no blood is circulated in patient's heart, no gas exchange is performed in the patient's body, and blood circulation and gas exchange for the blood are performed (oxygen is added and/or carbon dioxide is removed) by an extracorporeal circulator and an extracorporeal circulation (auxiliary circulation) in which blood is circulated in patient's heart, gas exchange is performed in the patient's body, and blood circulation and gas exchange for the blood are performed also by the extracorporeal circulator.

The structure of the bubble removing unit 1A will be described with reference mainly to FIG. 1. As shown in FIG. 1, the bubble removal unit 1A is for removing bubbles mixed in blood. The bubble removing unit 1A includes a unit body 40, a bubble reservoir 5 disposed at the upper part of the unit body 40 (circulation-flow forming chamber 2), a vacuum chamber 8 disposed on the bubble reservoir 5, a liquid reservoir 15 communicating with the vacuum chamber 8 through a connecting pipe 18, a first filter (filter member (deaerator film)) 9 that partitions the bubble reservoir 5 and the vacuum chamber 8 from each other, a second filter 16 disposed in the liquid reservoir 15, and a detection means (bubble detection means) 17A that detects the fluid level of the blood in the bubble reservoir 5.

The materials of the unit body 40, the bubble reservoir 5, the vacuum chamber 8, the connecting pipe 18, and the liquid reservoir 15 are not particularly limited; however, relatively hard resin materials such as polycarbonate, acrylic resin, polyethylene terephthalate, polyethylene, polypropylene, polystyrene, polyvinyl chloride, an acryl-styrene copolymer, and an acryl-butadiene-styrene copolymer are desirable. Moreover, substantially transparent materials are desirable so that the state of inside blood can be viewed.

The unit body 40 includes the circulation-flow forming chamber 2, an inlet port 3 for introducing blood into the circulation-flow forming chamber 2 (inner space), an outlet port 4 for discharging the blood in the circulation-flow forming chamber 2 out from the bubble removing unit 1A, and a first communicating section 6 and a second communicating section 7 for communicating the circulation-flow forming chamber 2 and the bubble reservoir 5 with each other.

The circulation-flow forming chamber 2 has a rotor-shaped inner space, that is, a substantially-circular-cross-section inner space, which causes the influent blood to form a circulation flow. The bubble removing unit 1A is used with the central axis 20 of the circulation-flow forming chamber 2 directed vertically. Thus, the plane perpendicular to the central axis 20 of the circulation-flow forming chamber 2 is herein referred to as a horizontal plane.

The circulation-flow forming chamber 2 has a disc-shaped large-diameter portion 21 located at the same height as the inlet port 3, a truncated conical portion 22 disposed on the large-diameter portion 21, and a body 23 disposed under the large-diameter portion 21.

The inner space of the truncated conical portion 22 is substantially shaped like a truncated cone whose inside diameter decreases upward gradually. Although the inner space of the truncated conical portion 22 in the drawing has an almost complete truncated cone shape, the inner space of the truncated conical portion 22 of the invention may not necessarily have a complete truncated cone shape, and its peripheral surface may be round as viewed from the side.

The inner space of the large-diameter portion 21 is substantially shaped like a disc whose inside diameter is larger than that of the lower end of the truncated conical portion 22.

The inner space of the body 23 has a substantially cylindrical shape (substantially columnar shape) whose inside diameter is smaller than that of the large-diameter portion 21. The lower part of the body 23 is shaped like a funnel, from the lower end of which the outlet port 4 projects.

The inlet port 3 projects in a direction tangential to the inner periphery of the large-diameter portion 21 of the circulation-flow forming chamber 2 (see FIG. 2).

The structure of the unit body 40 allows the blood flowing from the inlet port 3 into the circulation-flow forming chamber 2 to surely form a circulation flow.

The bubble reservoir 5 is for temporarily storing bubbles that have risen from the circulation-flow forming chamber 2. The bubble reservoir 5 is filled with blood when no bubbles are contained in the blood flowing into the circulation-flow forming chamber 2.

The bubble reservoir 5 has a substantially disc-shaped inner space. The upper surface of the bubble reservoir 5 is partitioned (covered) by the first filter 9. This substantial disc shape of the bubble reservoir 5 allows the first filter 9 to have a sufficiently large area while decreasing priming volume, and prevents bubbles from remaining more reliably when priming is charged. The shape of the bubble reservoir 5 is not limited to the substantial disc shape but may be a polygonal plate.

The central axis 50 of the bubble reservoir 5 is eccentric to the left in FIG. 1, with respect to the central axis 20 of the circulation-flow forming chamber 2. This makes it easy for the bubbles flowing into the bubble reservoir 5 to be collected to one side (the eccentric side, to the left in FIG. 1) of the bubble reservoir 5, thus allowing the bubbles to efficiently pass through the first filter 9.

The central axis 50 of the bubble reservoir 5 has an inclination with respect to the central axis 20 of the circulation-flow forming chamber 2. The inclination is such that the bubble reservoir 5 is higher as the distance from the central axis 20 of the circulation-flow forming chamber 2 increases. This enables the bubbles flowing into the bubble reservoir 5 to be collected to one side of the bubble reservoir 5 more smoothly and quickly.

The inclination angle α of the central axis 50 of the bubble reservoir 5 with respect to the central axis 20 of the circulation-flow forming chamber 2 is not particularly limited; however, it is preferable that it range from 0 to 50°, and more preferable that it range from 5 to 20°.

The bottom 51 of the bubble reservoir 5 is shaped like a mortar that decreases in depth gradually toward the center.

The vicinity of the top of the truncated conical portion 22 of the circulation-flow forming chamber 2 (unit body 40) communicates with the bubble reservoir 5 through the first communicating section 6. The first communicating section 6 is a circular opening at the bottom 51 of the bubble reservoir 5 (see FIG. 3).

When blood forms a circulation flow in the circulation-flow forming chamber 2, the bubbles in the blood are collected to the center according to the difference in density of the gas and liquid by centrifugal force. The bubbles collected to the center further come to the surface by buoyancy into the bubble reservoir 5 through the first communicating section 6 (see the dotted line in FIG. 1).

The bubbles flowing into the bubble reservoir 5 gather to the higher part of the bubble reservoir 5 (to the left in FIG. 1) by buoyancy.

The circulation-flow forming chamber 2 and the bubble reservoir 5 communicate with each other also through the second communicating section 7. The second communicating section 7 is open to the peripheral wall (the side wall) of the truncated conical portion 22 on the left of FIG. 1. The second communicating section 7 communicates the part of the bubble reservoir 5 opposite to the first communicating section 6 with respect to the central axis 50 and the peripheral wall of the truncated conical portion 22 with each other.

Of course, the capacity of the bubble reservoir 5 is constant. Accordingly, when the bubbles that have surfaced from the circulation-flow forming chamber 2 flow into the bubble reservoir 5 through the first communicating section 6, the same amount of blood as the inflow bubbles need to be returned from the bubble reservoir 5 to the circulation-flow forming chamber 2 in place of the inflow bubbles.

Since the invention has the second communicating section 7, the blood in the bubble reservoir 5 can return to the circulation-flow forming chamber 2 through the second communicating section 7 as the bubbles that have risen from the circulation-flow forming chamber 2 flow into the bubble reservoir 5 through the first communicating section 6 (see the dotted line in FIG. 1).

Accordingly, when the bubbles that have risen from the circulation-flow forming chamber 2 flow into the bubble reservoir 5, a one-way flow can be formed in order of the truncated conical portion 22, the first communicating section 6, the bubble reservoir 5, the second communicating section 7, and the truncated conical portion 22. This allows the bubbles in the circulation-flow forming chamber 2 to be introduced into the bubble reservoir 5 efficiently, smoothly, and rapidly. The formation of the one-way flow prevents the blood from staying in the bubble reservoir 5, offering the side effect of preventing clotting of blood.

Since the second communicating section 7 communicates with the peripheral wall of the truncated conical portion 22, the vicinity of the outlet of the second communicating section 7 is relatively near the central axis 20. Thus, the flow rate of the circulation flow is relatively low at the outlet of the second communicating section 7, so that the blood exiting from the second communicating section 7 can smoothly enter the truncated conical portion 22 without backflow or disturbance of the circulation flow.

The outlet of the second communicating section 7 may be either perpendicular to the peripheral wall of the truncated conical portion 22 or tangential to the peripheral wall of the truncated conical portion 22, that is, along the circulation flow.

Without the second communicating section 7 unlike the invention, when the bubbles in the circulation-flow forming chamber 2 flow into the bubble reservoir 5 through the first communicating section 6, the blood returning from the bubble reservoir 5 to the circulation-flow forming chamber 2 would pass through the first communicating section 6 in the direction opposite to the bubbles, thus making the flow in the vicinity of the first communicating section 6 turbulent to hinder smooth passage of the bubbles.

The embodiment has a groove 53 one step deeper than the bottom 51 on the side opposite to the first communicating section 6 with respect to the central axis 50. The bottom of the groove 53, or a slope 52, is inclined downward with respect to the horizontal toward the second communicating section 7. Providing the slope 52 allows the blood in the bubble reservoir 5 to flow into the second communicating section 7 in the bubble reservoir 5 more smoothly and quickly.

While the grade β of the slope 52 is not particularly limited, it is preferably in the range from 0 to 90°, and more preferably, in the range from 5 to 40°.

The first filter 9 is a membrane configured to allow air (gas) to pass through and not to allow blood to pass through. It is preferable that the first filter 9 (and also the second filter 16) be processed so that the surface become hydrophobic or be a hydrophobic membrane.

Examples of the material of the hydrophobic membrane include polytetrafluoroethylene (PTFE), a copolymer of tetrafluoroethylene and hexafluoropropylene (FEP), a copolymer of tetrafluoroethylene and perfluoroalkylvinylether (PFA), polychlorotrifluoroethylene (PCTFE), polyvinylidene fluoride (PVDF), a copolymer of ethylene and tetrafluoroethylene (ETFE), a copolymer of ethylene and chlorotrifluoroethylene (ECTFE), and polypropylene (PP). The first filter 9 is preferably made of such a material that is made porous by drawing, microphase separation, electron-beam etching, sintering, or argon plasma emission.

The method for hydrophobing is not particularly limited; for example, the surface of the first filter 9 may be coated with a hydrophobic material.

The first filter 9 is perpendicular to the central axis 50 of the bubble reservoir 5. In other words, the first filter 9 inclines with respect to the plane (horizontal plane) perpendicular to the central axis 20 of the circulation-flow forming chamber 2. This allows the bubbles flowing into the bubble reservoir 5 to be transferred along the slope of the first filter 9 to one side of the bubble reservoir 5 (to the left in FIG. 1), enabling the bubbles to be collected more smoothly and quickly.

Since the first filter 9 allows the gas in the bubble reservoir 5 to pass through as described above, water vapor from the bubble reservoir 5 can pass through the first filter 9. The water vapor that has passed through the first filter 9 is condensed into liquid L, and can move along the slope of the first filter 9 to the side opposite to the bubbles (to the right in FIG. 1), that is, toward the liquid reservoir 15, allowing the liquid L to easily flow into the liquid reservoir 15.

The vacuum chamber 8 has a platy (flat) inner space partitioned from the bubble reservoir 5 by the first filter 9. The vacuum chamber 8 is concentric with the bubble reservoir 5. Accordingly, the central axis of the vacuum chamber 8 also inclines with respect to the central axis 20 of the circulation-flow forming chamber 2. This allows the liquid L in the inner space of the vacuum chamber 8 to move toward the liquid reservoir 15, so that the liquid L can easily flow into the liquid reservoir 15, as in the above.

No blood flows into the vacuum chamber 8. In other word, the upper surface 91 of the first filter 9 is not in contact with blood, while the lower surface 92 is in contact with blood.

The bubbles (air) accumulated in the bubble reservoir 5 pass through the first filter 9 into the vacuum chamber 8, and are discharged (removed) out of the bubble removing unit 1A through a vent 153 of the liquid reservoir 15.

As shown in FIG. 1, the connecting pipe 18 projects from the lower part of the inclined vacuum chamber 8.

It is preferable that there be no step between the bottom 181 of the connecting pipe 18 and the upper surface 91 of the first filter 9, in other words, the bottom 181 of the connecting pipe 18 and the upper surface 91 of the first filter 9 be flush with each other. This prevents the liquid L from staying in the vacuum chamber 8, that is, allows the liquid L to smoothly flow from the upper surface 91 of the first filter 9 to the bottom 181 of the connecting pipe 18, ensuring that the liquid L is discharged toward the liquid reservoir 15.

The vacuum chamber 8 is connected to (provided with) the liquid reservoir 15 through the connecting pipe 18.

The liquid reservoir 15 includes a reservoir body 151, a check-valve mount portion 152 where a check valve 30 is mounted, and the vent 153 connected to deaerator means (not shown). The deaerator means may be a wall suction, for example. The wall suction is one of piping installation for sucking medical gas such as oxygen, medical air, or nitrogen, which is a suction (deaeration) pipe installed on the wall of an operating room. Another deaerator means is an individual vacuum pump. The operation of such deaerator means provides sucking force for sucking the vacuum chamber 8, allowing removing (sucking) of bubbles from the vacuum chamber 8.

The reservoir body 151 is shaped like a box. The reservoir body 151 can store the liquid L flowing out of the vacuum chamber 8 through the connecting pipe 18. This ensures holding of the liquid L in the reservoir body 151 (the liquid reservoir 15), thus surely preventing the liquid L from flowing out of the bubble removing unit 1A.

The check-valve mount portion 152 is a cylindrical part disposed at the upper part 155 of the reservoir body 151. The check-valve mount portion 152 inclines in the same orientation as that of the projection (formation) of the connecting pipe 18.

The check-valve mount portion 152 has at an end 154 the cylindrical vent 153 projecting therefrom. The presence of the vent 153 ensures and facilitates connecting the tube of the deaerator means to the vent 153, thus maintaining the vacuum chamber 8 under negative pressure to allow the gas (air) in the vacuum chamber 8 to be discharged from the vent 153.

The orientation of the projection of the vent 153 is substantially the same as that of the connecting pipe 18 (the check-valve mount portion 152). The vent 153 is smaller in outside diameter and inside diameter than the check-valve mount portion 152.

The bubble removing unit 1A has the second filter 16 and the check valve 30. The second filter 16 is a membrane configured to allow air (gas) to pass through and not to allow the liquid L to pass through substantially as with the first filter 9. The check valve 30 is a valve configured to allow gas to flow only toward the deaerator means.

The second filter 16 is disposed between the vacuum chamber 8 and the deaerator means, that is, close to the upper part 155 with respect to an opening 182 of the connecting pipe 18 of the reservoir body 151. In other words, the reservoir body 151 is disposed between the first filter 9 and the second filter 16.

This arrangement allows the liquid L from the connecting pipe 18 to flow into the reservoir body 151 without contact with the second filter 16, thereby allowing the liquid L to be held in the reservoir body 151 without fail to prevent the liquid L from flowing out of the bubble removing unit 1A with reliability.

The second filter 16 is substantially parallel to the first filter 9, that is, inclined with respect to the horizontal. Since the second filter 16 is disposed in this position, in case the liquid L comes into contact with the second filter 16, the liquid L is smoothly separated from the inclined second filter 16 (at angle β) along it, preventing a loss in the permeability (bubble removing capability) of the second filter 16.

The second filter 16 is located higher than the first filter 9 along the thickness or along the central axis 50. In other words, the second filter 16 is at the uppermost end 161 lower than the uppermost end 93 of the first filter 9, and at the lowermost end 162 substantially at the same height as the lowermost end 94 of the first filter 9.

The first filter 9 and the second filter 16 are disposed in different positions along the planes, that is, in the orientation perpendicular to the central axis 50 (the orientation of inclination). This prevents the liquid L on the first filter 9 from coming into contact with the second filter 16.

The check valve 30 is disposed between the vent 153 and the second filter 16, that is, in the check-valve mount portion 152. This prevents the gas discharged by the deaerator means from flowing backward to the vacuum chamber 8 without fail, ensuring removing the gas from the bubble removing unit 1A, and moreover, allows the negative pressure in the liquid reservoir 15 to be maintained with stability.

While the check valve 30 of the embodiment is a duckbill valve (see FIG. 1), the check valve 30 may not necessarily be that provided it allows only the gas flowing toward the deaerator means.

With the bubble removing unit 1A in which the truncated conical portion 22 is disposed at the upper part of the circulation-flow forming chamber 2, bubbles can be efficiently collected through the effective use of centrifugal force and buoyancy, and the collected bubbles can be efficiently sent to the bubble reservoir 5 through the first communicating section 6.

Past experience of the inventor indicates that the bubbles gathered to the center by the action of the circulation flow in the circulation-flow forming chamber 2 become a substantially columnar mass, the bubble mass having substantially the same diameter as the inside diameter $d_2$ of the first communicating section 6. Accordingly, when the inside diameter $d_2$ of the first communicating section 6 and the maximum inside diameter of the circulation-flow forming chamber 2 are approximate to each other or when the inside diameter $d_2$ of the first communicating section 6 is larger than the maximum diameter of the circulation-flow forming chamber 2, the bubble mass will spread into the entire circulation-flow forming chamber 2, resulting a decrease in the efficiency of separating the gas from the liquid.

From this point of view, preferably, the ratio $d_1:d_2$ of the inside diameter (the maximum diameter) $d_1$ of the body 23 of the circulation-flow forming chamber 2 to the inside diameter of the first communicating section 6 ranges from 1:1 to 10:1, and more preferably, from 2:1 to 4:1.

The vertex θ of the truncated conical portion 22 is preferably in the range from 10 to 170°, and more preferably, from 30 to 150°, further preferable, from 40 to 120°.

When the vertex θ of the truncated conical portion 22 is too large, the truncated conical portion 22 becomes low in height, thus making it difficult to introduce the bubbles into the bubble reservoir 5 through effective use of buoyancy; in contrast, when the vertex θ of the truncated conical portion 22 is too small, the truncated conical portion 22 becomes high in height, thereby increasing the priming volume.

The body 23 of the circulation-flow forming chamber 2 contains a disc 11 for defining the lower end of the bubble mass gathered to the center and a connecting member 12 for connecting the disc 11 to the bottom of the circulation-flow forming chamber 2. The disc 11 is disposed in the position perpendicular to the central axis 20 of the circulation-flow forming chamber 2. Although it is preferable that the disc 11 be concentric to the circulation-flow forming chamber 2, it may be eccentric therefrom.

Since the presence of the disc 11 prevents the bubble mass from being formed below the disc 11, the gathered bubble mass can be more reliably prevented from flowing out through the outlet port 4.

The height of the upper surface of the disc 11 is set substantially the same as that of the lower end 31 of the inlet port 3 or lower. This prevents the disc 11 from interfering with the formation of circulation flow.

The diameter of the disc 11 is set substantially the same as or larger than that of the inside diameter of the first communicating section 6. Since the diameter of the bubble mass is substantially the same as the inside diameter of the first communicating section 6 as described above, the diameter of the disc 11 becomes larger than that of the bubble mass by setting the diameter of the disc 11 larger than the inside diameter of the first communicating section 6, thereby more reliably preventing the bubble mass from being formed below the disc 11.

The disc 11 is fixed to the upper end of the connecting member 12. The connecting member 12 is a cylindrical member having substantially the same diameter as that of the disc 11, and is fixed at the lower end to the bottom of the circulation-flow forming chamber 2. The peripheral wall of the connecting member 12 has a plurality of slits or openings, through which blood flows from the outer periphery of the connecting member 12 toward the inner periphery, and further to the outlet port 4.

The slits or openings of the connecting member 12 may have a filter impervious to bubbles. The connecting member 12 may be a member such as a leg for solely supporting the disc 11.

The cross-sectional area of the donut-shaped (cylindrical) channel between the outer peripheral surface of the disc 11 and the connecting member 12 and the inner peripheral surface of the body 23 is set larger than the cross-section area of the inlet port 3. This reduces the resistance of the donut-shaped channel.

The bubble removing unit 1A includes a detection means 17A for detecting the bubbles mixed in the blood or for detecting the fluid level of the blood in the bubble reservoir 5. The detection means 17A includes a first sensor 13A disposed outside the upper part 521 of the slope 52 (the groove 53) (see FIGS. 1 and 2).

Referring to FIG. 2, the first sensor 13A includes an ultrasonic transmitter (transmitter) 131 and an ultrasonic receiver (receiver) 132 disposed opposite to the ultrasonic transmitter 131 with the groove 53 in between. The first sensor 13A receives ultrasonic waves sent from the ultrasonic transmitter 131 with the ultrasonic receiver 132, and determines whether the substance between the ultrasonic transmitter 131 and the ultrasonic receiver 132 is blood (liquid phase) or bubbles (gas phase) by using the difference in transmittance of ultrasonic waves between liquid (blood) and gas (bubbles). In other words, when bubbles are collected into the bubble reservoir 5, so that the fluid level is decreased to the position of the first sensor 13A, the fluid level can be detected by the first sensor 13A.

One sensor can be used both as the ultrasonic transmitter 131 and the ultrasonic receiver 132, in which case it can be disposed to one side of the groove 53 as viewed from the bottom.

The first sensor 13A is not limited to the foregoing ultrasonic sensor but may be of another system such as optical sensor.

The bubble removing unit 1A allows the bubbles mixed in the extracorporeal circulator 100A to be removed reliably and prevents the liquid that has passed through the first filter 9 (for example, condensation of water vapor) from flowing out of the bubble removing unit 1A with the second filter 16 without fail.

Referring to FIG. 4, the extracorporeal circulator 100A will be described.

The extracorporeal circulator 100A comprises a centrifugal pump (blood pump) 101 for feeding blood, a venous line 102 connecting the inlet port of the centrifugal pump 101 with a patient, an arterial line 103 connecting the outlet port of the centrifugal pump 101 with the patient, the bubble removing unit 1A disposed in the middle of the venous line 102, an artificial lung (artificial lung section) 104 disposed in the middle of the arterial line 103, for exchanging gas for blood, a flowmeter 105 disposed in the middle of the arterial line 103, a recirculating line (bypass line) 106, clamps 107, 108, and 109 that open or close the channel by clamping or opening the tubes of the line, and a controller (blood-feed control means (control means)) 110 for controlling the open and close of the clamps 107, 108, and 109 in response to the detection signal (detection result) from the first sensor 13A of the bubble removing unit 1A.

As shown in FIG. 4, in the extracorporeal circulator 100A, the blood generally passes through the venous line 102, the bubble removing unit 1A, the centrifugal pump 101, the artificial lung 104, the arterial line 103, and the flowmeter 105, and returns to the patient. That is, in the extracorporeal circulator 100A, the blood generally flows along the arrow in FIG. 4. Such a flow of blood (circulation of blood) is hereinafter referred to as "normal circulation".

In the extracorporeal circulator 100A, the bubble removing unit 1A is disposed upstream from the centrifugal pump 101. This prevents the bubbles mixed in the blood from being broken into small pieces by the centrifugal pump 101, ensuring separation and removal of the bubbles from the blood.

The artificial lung 104 has a blood inlet port (inlet) 104b through which blood flows into the artificial lung 104, a blood outlet port (outlet) 104a through which blood flows out of the artificial lung 104, a gas inlet port 104c, a gas outlet port (not shown), a heating-medium inlet port 104d, and a heating-medium outlet port 104e projecting therefrom.

In the extracorporeal circulator 100A, the blood inlet port 104b is located close to (connected to) the centrifugal pump 101 (discharge port 101a), and the blood outlet port 104a is located close to (connected to) the patient. That is, the artificial lung 104 of the extracorporeal circulator 100A is disposed between the discharge port 101a through which the blood in the centrifugal pump 101 is discharged and an inlet port 106a into which the blood in the recirculating line 106 flows.

The recirculating line 106 connects the upper stream of the centrifugal pump 101, that is, the venous line 102 in the vicinity of the suction port of the centrifugal pump 101 to the arterial line 103 in the vicinity of the outlet port 104a of the artificial lung 104 by a short circuit. This allows the blood discharged from the outlet port 104a of the artificial lung 104 to return to the centrifugal pump 101 without returning to the patient, that is, while bypassing the patient. Such a blood flow between the centrifugal pump 101 and the recirculating line 106 is hereinafter referred to as "recirculation".

Since the artificial lung 104 is disposed between the discharge port 101a of the centrifugal pump 101 and the inlet port 106a of the recirculating line 106, recirculating blood can be subjected to gas exchange with reliability.

The clamp 107 is disposed in the venous line 102 in the vicinity of the outlet port 4 of the bubble removing unit 1A; the clamp 108 is disposed in the arterial line 103 in the vicinity of the artificial lung 104; and the clamp 109 is disposed in the recirculating line 106.

The vent 153 of the bubble removing unit 1A is connected to the wall suction (deaeration means) through a deaerating line 111. In the middle of the deaerating line 111, a negative-pressure regulator 112 for regulating the pressure in the vacuum chamber 8 is provided.

The controller 110 normally controls the clamps 107 and 108 so as to be opened and the clamp 109 so as to be closed. This enables the extracorporeal circulator 100A to perform normal circulation.

Upon activation of the centrifugal pump 101, the blood aspirated from the patient via a venous catheter (not shown) first passes through the venous line 102 into the inlet port 3 of the bubble removing unit 1A. The bubble removing unit 1A removes bubbles in the blood as described above. The blood from which bubbles are removed flows out of the outlet port 4 of the bubble removing unit 1A and passes through the centrifugal pump 101 into the artificial lung 104. The artificial lung 104 executes gas exchange (adding oxygen and taking out carbon dioxide) to the blood. The oxygenated blood (that has passed through the artificial lung 104) passes through the arterial line 103 and is returned (sent) to the patient via an arterial catheter (not shown).

In contrast, when the first sensor 13A of the bubble removing unit 1A detects that a predetermined amount of bubbles is accumulated in the bubble reservoir 5, that is, the fluid level of the blood, the controller 110 controls the bloodstream (the volume of blood flow (the rate of blood flow)) so as not to feed the bubbles to the patient. In other words, the controller 110 controls the clamps 107 and 108 so as to be closed and the clamp 109 so as to be opened. Thus, the blood exiting from the artificial lung 104 is returned to the inlet port of the centrifugal pump 101 through the recirculating line 106. The blood thus repeatedly circulates or recirculates a cyclic channel including the centrifugal pump 101 and the artificial lung 104.

The recirculation prevents the bubbles in the bubble removing unit 1A from being fed to the patient with reliability, and prevents damage to the blood in the centrifugal pump 101 even when the centrifugal pump 101 is continuously operated.

During recirculation, when the first sensor 13A detects that the bubbles in the bubble reservoir 5 are sucked into the vacuum chamber 8, so that the bubbles in the bubble reservoir 5 are reduced or eliminated, that is, when the blood level increases and the first sensor 13A does not detect the fluid level of blood, the controller 110 returns the clamps 107 and 108 to the open state and the clamp 109 to the closed state to recover the normal circulation.

Thus, the extracorporeal circulator 100A can execute smooth and appropriate extracorporeal circulation while reliably preventing excessive bubble accumulation in the bubble reservoir 5.

The extracorporeal circulator 100A (the bubble removing unit 1A) can reliably prevent the bubbles mixed in the blood from being sent to the patient while reducing the priming volume thereof, as described above.

The vacuum chamber 8 is connected to the deaeration means so as to be maintained in negative pressure, that is, to be sucked. The vacuum chamber 8 of the extracorporeal circulator 100A may be subjected to sucking force either constantly or only when the fluid level of the blood is detected by the first sensor 13A.

In any case, the extracorporeal circulator 100A can remove the bubbles from the vacuum chamber 8 (the bubble removing unit 1A) without fail. This is advantageous.

Second Embodiment

Figure 5:
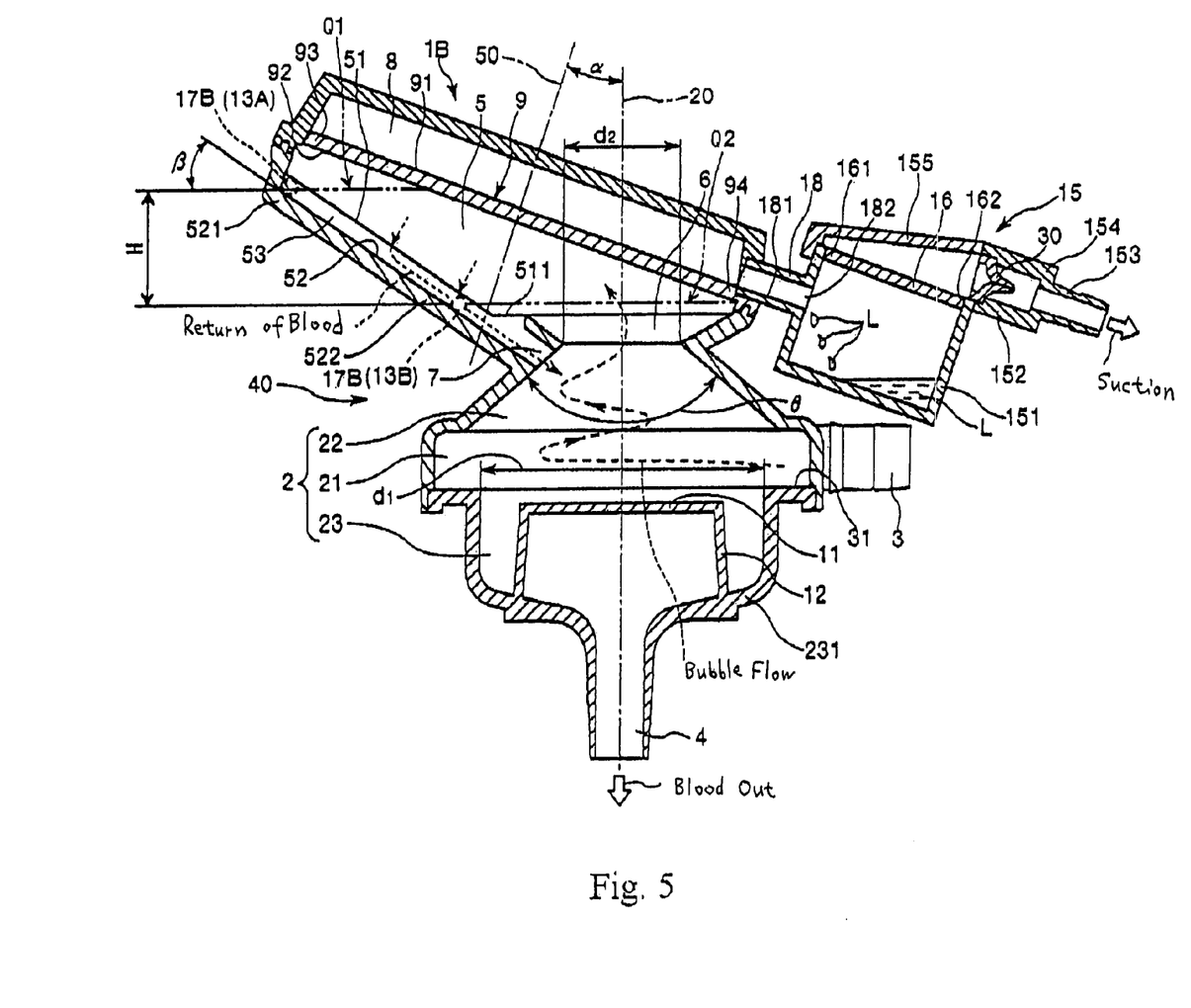
FIG. 5 is a cross-sectional side view of a bubble removing unit of an extracorporeal circulator (a second embodiment) of the invention.
Figure 6:
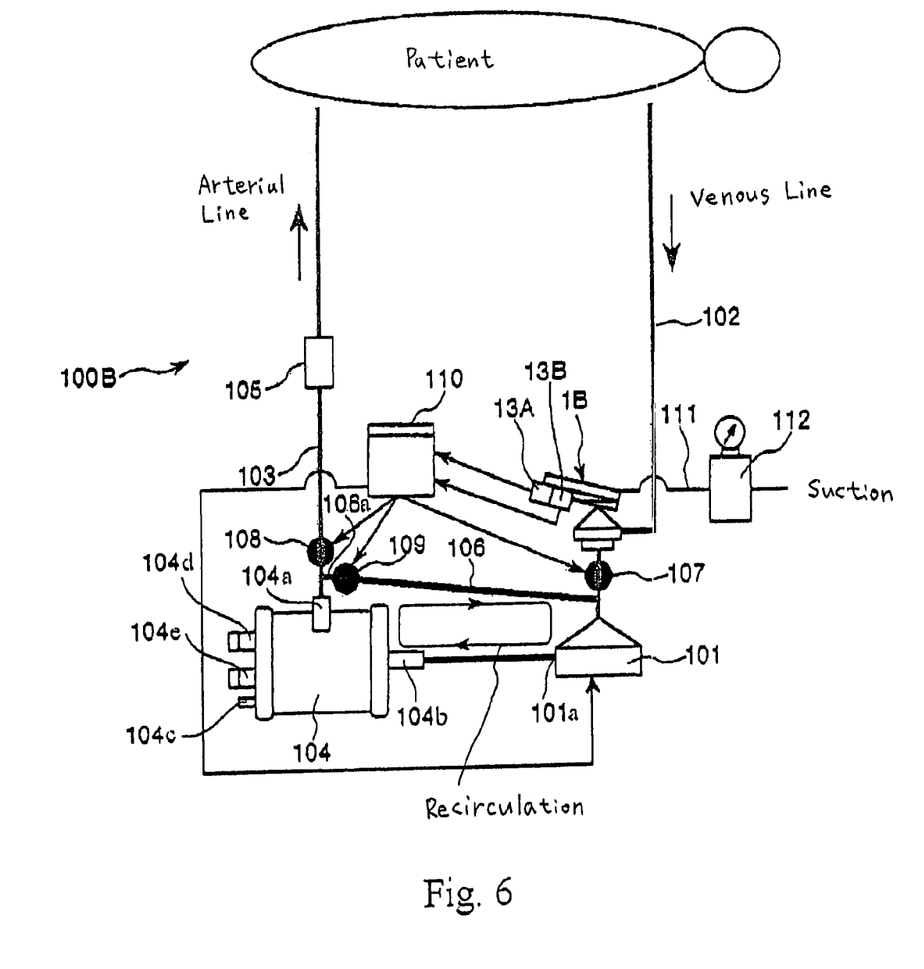
FIG. 6 is a schematic diagram of the extracorporeal circulator according to the second embodiment of the invention.
Figure 7:
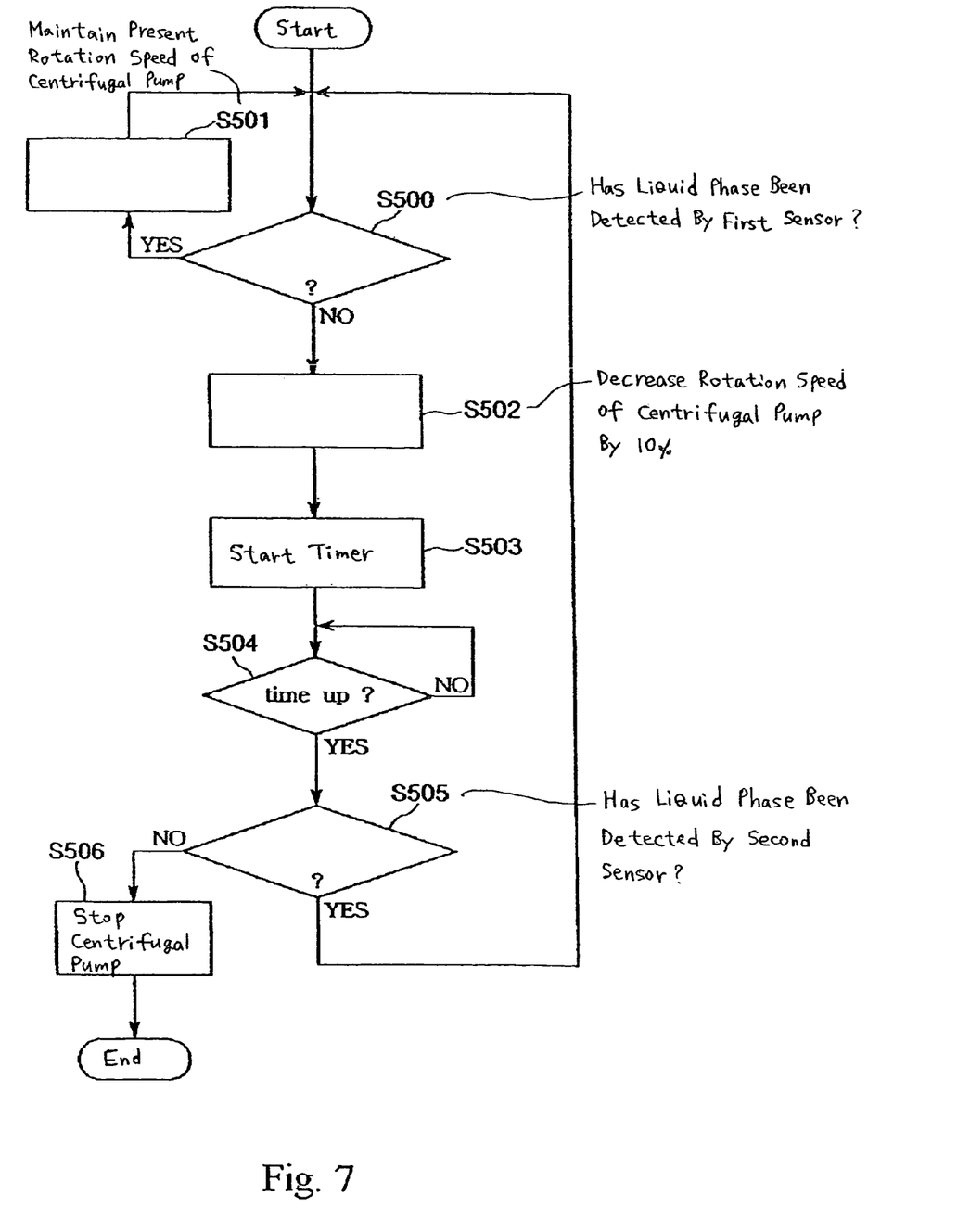
FIG. 7 is a flowchart of the control program of a controller of the extracorporeal circulator of FIG. 6.
Figure 8:
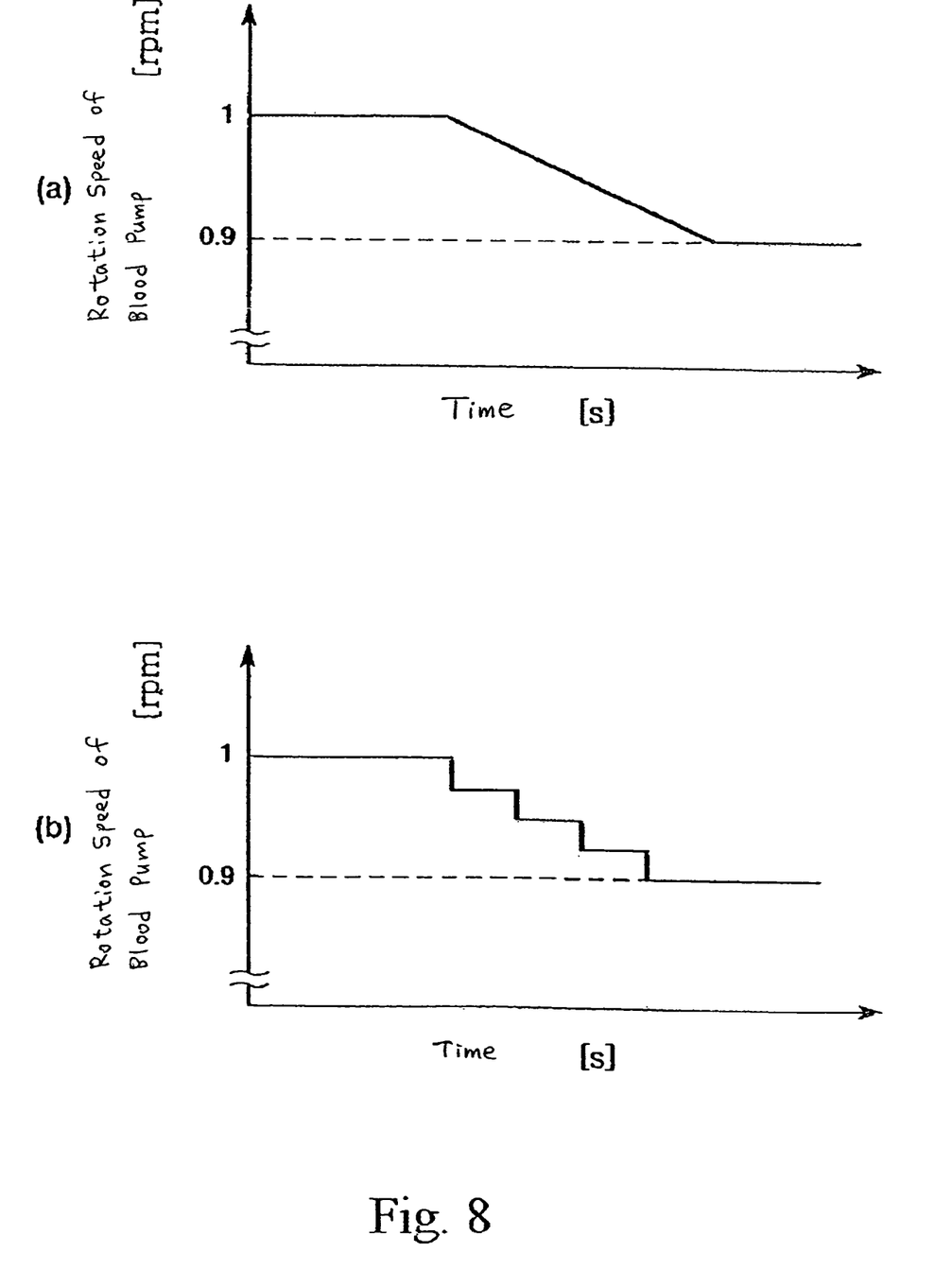
FIG. 8 is a graph showing changes in the rotation speed of the blood pump with time under the control of the controller of the extracorporeal circulator of FIG. 6.

FIG. 5 is a cross-sectional side view of a bubble removing unit of an extracorporeal circulator (a second embodiment) of the invention; FIG. 6 is a schematic diagram of the extracorporeal circulator according to the second embodiment of the invention; FIG. 7 is a flowchart of the control program of a controller of the extracorporeal circulator of FIG. 6; and FIG. 8 is a graph showing changes in the rotation speed of the blood pump with time under the control of the controller of the extracorporeal circulator of FIG. 6. The upper part in FIG. 5 is referred to as "the upper part" or "above", and the lower part is referred to as "the lower part" or "below" for the convenience of description.

The extracorporeal circulator of the embodiment of the invention will be described with reference to the drawings, in which the embodiment will be described hereinbelow with particular emphasis on differences from the above-described embodiment, and descriptions of like or corresponding parts will be omitted.

The embodiment is the same as the first embodiment except the structure of the detection means of the bubble removing unit.

Referring to FIG. 5, a bubble removing unit 1B includes a detection means 17B for detecting the fluid level of the blood in the bubble reservoir 5. The detection means 17B includes a first sensor 13A and a second sensor 13B.

The first sensor 13A and the second sensor 13B each include the ultrasonic transmitter 131 and the ultrasonic receiver 132 like the first sensor 13A of the first embodiment. The first sensor 13A is a sensor for detecting a first blood fluid level Q1; and the second sensor 13B is a sensor for detecting a second fluid level Q2 lower than the first fluid level.

The first sensor 13A is disposed outside the upper part 521 of the slope 52. The second sensor 13B is disposed outside the center of the slope 52. In other words, the first sensor 13A and the second sensor 13B are disposed along the inclination of the slope 52. This ensures detection of changes in fluid level with the flow of the blood along the slope 52.

The first sensor 13A and the second sensor 13B are separate from each other by distance H in the vertical direction, that is, along the central axis 20. While the distance H is not particularly limited, it is preferably in the range from 3 to 30 mm, and more preferably, from 5 to 20 mm.

When the distance H is less than the lower limit, the first sensor 13A and the second sensor 13B are too close to each other. Accordingly, after the first sensor 13A detects the first fluid level Q1, the second sensor 13B detects the second fluid level Q2 soon to stop the operation of the centrifugal pump 101. This sometimes extremely reduces the operability of the extracorporeal circulator 100B.

On the other hand, when the distance H exceeds the upper limit, the second sensor 13B may be located lower than the lowermost surface 511 of the bubble reservoir 5 depending on other conditions (for example, when the bubble reservoir 5 is small). This sometimes makes it impossible for the second sensor 13B to detect the second fluid level Q2 in the bubble reservoir 5.

The extracorporeal circulator 100B will then be described.

The extracorporeal circulator 100B is similar to the extracorporeal circulator 100A of the first embodiment except that the controller 110 controls the operation of the centrifugal pump 101 on the basis of the information (detection results) obtained from the first sensor 13A and the second sensor 13B.

The controller 110 normally controls the clamps 107 and 108 so as to be open and the clamp 109 so as to be closed. This enables the extracorporeal circulator 100B to perform normal circulation.

Upon activation of the centrifugal pump 101, the blood drawn from the patient via a venous catheter (not shown) first passes through the venous line 102 into the inlet port 3 of the bubble removing unit 1B. The bubble removing unit 1B removes bubbles in the blood in the same manner as the bubble removing unit 1A of the first embodiment. The blood from which bubbles are removed flows out of the outlet port 4 of the bubble removing unit 1B and passes through the centrifugal pump 101 into the artificial lung 104. The artificial lung 104 executes gas exchange (adding oxygen and taking out carbon dioxide) to the blood. The oxygenated blood passes through the arterial line 103 and is returned (sent) to the patient via an arterial catheter (not shown).

With the extracorporeal circulator 100B, when the amount of the bubbles flowing into the bubble removing unit 1B together with the venous blood matches the bubble removing capacity of the bubble removing unit 1B (bubble removing means), the fluid level in the extracorporeal circulator 100B becomes stable (is balanced) at a position in the bubble reservoir 5.

With the extracorporeal circulator 100B (the bubble removing unit 1B), when the rotation speed of the centrifugal pump 101 is decreased, the amount of blood being drawn is reduced, so that the amount of inflow bubbles is decreased. Accordingly, the bubble removing capacity exceeds the inflow bubbles, so that the bubbles in the bubble reservoir 5 are removed in sequence. Thus, the blood in the bubble reservoir 5 shows a tendency to increase in fluid level. In contrast, when the rotation speed of the centrifugal pump 101 is excessively increased, the centrifugal pump 101 operates (works) so as to withdraw an excessive amount of patient's blood, so that the centrifugal pump 101 withdraws not only the blood but also air. This results in an increase in the amount of inflow bubbles, so that the bubbles exceed the bubble removing capacity of the bubble removing unit 1B (bubble removing means). Thus, the bubbles are accumulated in the bubble reservoir 5 to lower the fluid level of the blood.

It is ideal for the extracorporeal circulator 100B to locate (maintain) the fluid level of the blood in the bubble reservoir 5 hither than the first fluid level Q1.

Accordingly, when the fluid level falls from a position higher than the first fluid level Q1 to a position between the first fluid level Q1 and the second fluid level Q2, the controller 110 decreases (reduces) the rotation speed of the centrifugal pump 101 so that the fluid level rises higher than the first fluid level Q1.

When the fluid level between the first fluid level Q1 and the second fluid level Q2 further falls to a position lower than the second fluid level Q2, this indicates that the bubble reservoir 5 becomes filled with a large amount of bubbles. This makes it difficult to remove the bubbles from the bubble removing unit 1B under the control of the centrifugal pump 101 with this rotation speed. Therefore, the controller 110 stops the operation of the centrifugal pump 101. After the centrifugal pump 101 is stopped, the bubbles in the bubble removing unit 1B are quickly removed, and then the centrifugal pump 101 is again started quickly. That is, the extracorporeal circulation (normal circulation) is recovered quickly.

Since no new bubbles enter the bubble removing unit 1B while the centrifugal pump 101 is out of operation, the bubbles in the bubble removing unit 1B are reliably removed.

The control program of the controller 110 of the extracorporeal circulator 100B will be described mainly with reference to the flowchart of FIG. 7.

As described above, when the extracorporeal circulation is started, the program determines whether a fluid phase is sensed by the first sensor 13A, that is, whether the fluid level is lower than the first fluid level Q1 (step S500), wherein when a fluid phase is sensed by the first sensor 13A (the fluid level is higher than the first fluid level Q1), the (present) rotation speed of the centrifugal pump 101 at that time is maintained (step S501).

After the execution of step S501, the program returns to step S500, and the subsequent steps are executed in sequence.

In step S500, when it is determined that no fluid phase has been sensed by the first sensor 13A (the fluid level has fallen to the first fluid level Q1), the rotation speed of the centrifugal pump 101 at that time is decreased by a predetermined degree (the rate of decrease) (in this embodiment, 10 percent) (step S502).

Then, the timer built in the controller 110 is started (step S503), wherein when it is determined by the timer that a predetermined time has passed (step S504), it is determined whether a fluid phase has been sensed by the second sensor 13B (step S505).

In step S505, when it is determined that a fluid phase is sensed by the second sensor 13B (the fluid level has not fallen to the second fluid level Q2), the program returns to step S500, and the subsequent steps are executed in sequence.

On the other hand, when it is determined in step S505 that the second sensor 13B has sensed no fluid phase (the fluid level has fallen to the second fluid level Q2), the program stops the operation of the centrifugal pump 101 (step S506).

Thus, the extracorporeal circulator 100B can execute smooth and appropriate extracorporeal circulation while reliably preventing excessive bubble accumulation in the bubble reservoir 5. Moreover, the extracorporeal circulator 100B (the bubble removing unit 1B) can reliably prevent the bubbles mixed in the blood from being sent to the patient while reducing the priming volume, as in the extracorporeal circulator 100A of the first embodiment.

Although the rotation speed of the centrifugal pump 101 is controlled so as to decrease by 10 percent by one process of step S502 and the timer is set, the decrease may be either continuous as shown in FIG. 8(a) or stepwise as shown in FIG. 8(b) according to the combination of step S502 and S503.

When the rotation speed is controlled so as to decrease continuously, the rotation speed can be decreased quickly in a state in which the amount of inflow bubbles significantly exceeds the bubble removing capacity. Thus, the extracorporeal circulation can be maintained without the need for stopping the centrifugal pump 101.

In contrast, when the rotation speed is controlled so as to decrease stepwise, the time to recover the fluid level (from falling to rising) is given in a state in which the amount of inflow bubbles a little exceeds the bubble removing capacity. This eliminates the need for excessively decreasing the rotation speed of the centrifugal pump 101 (blood pump).

In step S502, the rate of decrease in the rotation speed of the centrifugal pump 101 is not limited to 10 percent; it is preferably in a predetermined range from 5 to 90 percent, and more preferably in a predetermined range from 10 to 50 percent.

In step S505, it is determined that no liquid phase is sensed by the second sensor 13B, the operation of the centrifugal pump 101 is stopped. However, the invention is not limited to that; for example, the controller 110 may control the clamps 107 and 108 so as to be closed and the clamp 109 so as to be opened without stopping the operation of the centrifugal pump 101. This allows the blood exiting from the artificial lung 104 to be returned to the inlet port of the centrifugal pump 101 through the recirculating line 106. Thus the blood repeatedly circulates, or recirculates through the cyclic channel including the centrifugal pump 101 and the artificial lung 104. The recirculation prevents the bubbles in the bubble removing unit 1B from being fed to the patient with reliability and prevents damage to the blood in the centrifugal pump 101 even when the centrifugal pump 101 is continuously operated.

During recirculation, the bubbles in the bubble removing unit 1B are quickly removed, and then the clamps 107 and 108 are returned to the open state, and the clamp 109 is returned to the closed state, that is, the recirculation is stopped, and the program is returned to normal extracorporeal circulation (normal circulation). Preferably, the timing to stop the recirculation is when (in the case where) the first sensor has sensed that the fluid level of the blood has reached the first fluid level.

Thus, the oxygenated blood can be returned (fed) to the patient by stopping the recirculation and recovering normal circulation.

As shown in FIG. 5, it is preferable that the second sensor 13B be disposed substantially at the same height as the lowermost end 94 of the first filter 9. This arrangement allows the operation of the centrifugal pump 101 to be stopped when the second sensor 13B senses the second fluid level Q2, thus preventing a further decrease in blood fluid level and the entire bubble reservoir 5 from being filled with air.

While the first sensor 13A and the second sensor 13B each have the ultrasonic transmitter 131 and the ultrasonic receiver 132, the invention is not limited to that; for example, one sensor may be used both as the ultrasonic transmitter 131 and the ultrasonic receiver 132 or both sensors may each be used both as the ultrasonic transmitter 131 and the ultrasonic receiver 132.

While the first sensor 13A and the second sensor 13B are ultrasonic sensors, the invention is not limited to that; for example, one may be of another system such as an optical sensor, or alternatively, both may be of another system such as an optical sensor.

While the extracorporeal circulator of the invention has been described with reference to the embodiments shown in the drawings, it is to be understood that the invention is not limited to those. The components of the extracorporeal circulator may be replaced with any component capable of similar function, and moreover, may also have any additional component.

While the detection means is configured to detect the fluid level of the blood in the bubble reservoir, the invention is not limited to that. The detection means may be configured to detect information on the fluid level (for example, pressure or mass).

The liquid reservoir may have an outlet port for discharging accumulated liquid. This allows the accumulated liquid to be discharged from the bubble reservoir before the liquid comes into contact with (reaches) the second titter.

While the outlet port is normally closed, it may be configured to be opened after surgery to remove the accumulated liquid.

The liquid reservoir may have means for cooling the interior of the liquid reservoir. This ensures condensation of water vapor in the liquid reservoir, thereby reliably preventing the water vapor from passing through the second filter. Examples of the cooling means include a heatsink and a Peltier device around the liquid reservoir body.

INDUSTRIAL APPLICABILITY

An extracorporeal circulator according to the invention comprises: a venous line for drawing blood from a patient; a blood pump for feeding the blood; an artificial lung that performs gas exchange of the blood; an arterial line for feeding the blood that has passed through the artificial lung to the patient; a bubble removing unit that removes the bubbles mixed in the blood; blood-feed control means for controlling the amount of blood being fed so as not to feed the bubbles to the patient; and a bypass line for bypassing the blood discharged from the blood pump and returning the blood to the blood pump. This arrangement can reliably prevent bubbles mixed in the blood from being fed to the patient while reducing the priming volume. This provides industrial applicability.

The invention claimed is:

1. An extracorporeal circulator comprising:
a venous line for receiving blood from a patient;
a blood pump for drawing the blood into the venous line;
an artificial lung that performs gas exchange of the blood;
an arterial line for returning the blood that has passed through the artificial lung to the patient;
a bubble removing unit that removes bubbles mixed in the blood and including a detection mechanism for detecting a state of bubble presence in the bubble removal unit;
blood-feed control means for controlling an amount of blood fed to the bubble removing unit;
a closable bypass line for bypassing the blood discharged from the blood pump and returning the blood to the blood pump; and
a by-pass opening and closing mechanism operably connected to the bubble detection mechanism and the blood-feed control means for opening and closing the by-pass line in response to a detection result received from the detection mechanism;

wherein the bubble removing unit comprises:

a circulation-flow forming chamber including an inner space having a substantially circular cross section;

an inlet disposed substantially tangential to an inner periphery of the circulation-flow forming chamber, for introducing the blood into the circulation-flow forming chamber so that the blood forms a circulation flow in the circulation-flow forming chamber;

an outlet disposed at a lower part of the circulation-flow forming chamber; and a bubble reservoir disposed on the circulation-flow forming chamber, for temporarily storing the bubbles rising from the circulation-flow forming chamber;

a first communicating section communicating a vicinity of a top of the circulation-flow forming chamber with the bubble reservoir to allow the bubbles rising from the circulation-flow forming chamber to pass through the first communicating section and into the bubble reservoir; and a second communicating section for communicating the vicinity of a peripheral wall of the circulation-flow forming chamber with the bubble reservoir, wherein the bubbles rising from the circulation-flow forming chamber flow into the bubble reservoir through the first communicating section and the blood in the bubble reservoir is returned to the circulation-flow forming chamber through the second communicating section.

2. A method of extracorporeal blood circulation comprising:

extracorporeally circulating blood which has been removed from a patient through operation of a pump while subjecting the blood to removal of bubbles that are temporarily stored in a bubble reservoir, and while subsequently subjecting the blood to gas exchange;

returning the blood which has been subjected to the bubble removal and the subsequent gas exchange to the patient; and controlling the extracorporeal circulation of the blood based on an amount of bubbles in the bubble reservoir so as not to feed bubbles to the patient, wherein the controlling of the extracorporeal circulation of the blood comprises:

reducing a speed of the pump from a set speed when the amount of bubbles in the bubble reservoir is greater than the predetermined amount; and returning the speed of the pump to the set speed when the amount of bubbles in the bubble reservoir is not greater than the predetermined amount.

3. The method according to claim 2, wherein reducing a speed of the pump includes stopping the pump.

4. A method of extracorporeal blood circulation comprising:

extracorporeally circulating blood which has been removed from a patient through operation of a pump at a set speed while subjecting the blood to removal of bubbles that are temporarily stored in a bubble reservoir, and while subsequently subjecting the blood to gas exchange;

returning the blood which has been subjected to the bubble removal and the subsequent gas exchange to the patient; and controlling the extracorporeal circulation of the blood based on an amount of bubbles in the bubble reservoir so as not to feed bubbles to the patient, wherein the controlling of the extracorporeal circulation of the blood comprises:

recirculating the blood after the gas exchange when the amount of bubbles in the bubble reservoir is greater than the predetermined amount so that the blood which has been subjected to the gas exchange is not returned to the patient; and returning the blood after the gas exchange to the patient when the amount of bubbles in the bubble reservoir is not greater than the predetermined amount.

5. The method according to claim 4, wherein the amount of bubbles in the bubble reservoir is determined by detecting a level of the blood in the bubble reservoir.

6. The method according to claim 4, wherein the blood from the patient is introduced into a chamber which communicates with the bubble reservoir, and wherein said predetermined amount of bubbles is a first predetermined amount, and further comprising controlling operation of the blood pump to reduce a rate at which blood is introduced into the chamber when the amount of bubbles in the bubble reservoir is greater than a second predetermined amount which is less than the first predetermined amount.

* * * * *